(12) United States Patent
Bourquin

(10) Patent No.: US 11,482,034 B2
(45) Date of Patent: Oct. 25, 2022

(54) DEVICE AND METHOD FOR PHYSIOLOGICAL PARAMETER DETECTION

(71) Applicant: KONINKLIJKE PHILIPS N.V., Eindhoven (NL)

(72) Inventor: Yannyk Parulian Julian Bourquin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 779 days.

(21) Appl. No.: 16/346,891

(22) PCT Filed: Nov. 7, 2017

(86) PCT No.: PCT/EP2017/078508
§ 371 (c)(1),
(2) Date: May 2, 2019

(87) PCT Pub. No.: WO2018/083351
PCT Pub. Date: May 11, 2018

(65) Prior Publication Data
US 2020/0193121 A1    Jun. 18, 2020

(30) Foreign Application Priority Data
Nov. 7, 2016   (EP) ..................... 16197460

(51) Int. Cl.
*A61B 5/1455*   (2006.01)
*H01L 33/50*   (2010.01)
(Continued)

(52) U.S. Cl.
CPC ........ *G06V 40/1318* (2022.01); *A61B 5/0059* (2013.01); *A61B 5/1455* (2013.01); *A61B 5/6826* (2013.01); *H01L 33/504* (2013.01)

(58) Field of Classification Search
CPC ....... A61B 5/0059–0091; A61B 5/1455–1464; A61B 5/02416–02444;
(Continued)

(56) References Cited

U.S. PATENT DOCUMENTS 7,982,229 B2    7/2011   Bechtel et al.
2007/0129613 A1   6/2007   Rochester et al.
(Continued)

FOREIGN PATENT DOCUMENTS

EP    2401958 A1    1/2012
EP    3020331 A1    5/2016
(Continued)

*Primary Examiner* — Thaddeus B Cox

(57) ABSTRACT

The present invention relates to a device and method for detecting light allowing retrieval of a physiological parameter of a user carrying said device. To improve the efficiency of light capturing, the device (1, 2, 3, 4) comprises a light source (10) arranged for emitting light of at least a first wavelength into tissue of the subject, a wavelength converter (20) arranged for receiving at least part of the emitted light after interaction of the emitted light with the tissue and for converting the received light into at least a second wavelength different from the first wavelength, and a light sensor (30) arranged for receiving light converted by said wavelength converter.

18 Claims, 3 Drawing Sheets

(51) Int. Cl.
*G06V 40/13* (2022.01)
*A61B 5/00* (2006.01)

(58) Field of Classification Search
CPC ............... A61B 5/0261; A61B 5/6826; H01L 33/50–508
See application file for complete search history.

(56) References Cited

U.S. PATENT DOCUMENTS

| | | |
|---|---|---|
| 2008/0039729 A1 | 2/2008 | Cho et al. |
| 2010/0049017 A1* | 2/2010 | LeBoeuf ............... A61B 5/6826 356/300 |
| 2010/0327306 A1 | 12/2010 | Van Der Burgt et al. |
| 2013/0131519 A1 | 5/2013 | LeBoeuf et al. |
| 2013/0215496 A1 | 8/2013 | Ban |
| 2014/0051955 A1 | 2/2014 | Tiao et al. |
| 2014/0107495 A1 | 4/2014 | Marinelli et al. |
| 2014/0058227 A1 | 7/2014 | Yamanaka |
| 2015/0094550 A1 | 4/2015 | Karp et al. |
| 2016/0079490 A1 | 3/2016 | De Boer |
| 2017/0303838 A1* | 10/2017 | Brill ................... G01N 21/6428 |

FOREIGN PATENT DOCUMENTS

| | | |
|---|---|---|
| JP | 2012125370 A | 7/2012 |
| WO | 2015197385 A1 | 12/2015 |
| WO | 2016066312 A1 | 5/2016 |
| WO | 2016066888 A1 | 5/2016 |

\* cited by examiner

DEVICE AND METHOD FOR PHYSIOLOGICAL PARAMETER DETECTION

This application is the U.S. National Phase application under 35 U.S.C. § 371 of International Application No. PCT/EP2017/078508, filed on 7 Nov. 2017, which claims the benefit of European Application Serial No. 16197460.5, filed 7 Nov. 2016. These applications are hereby incorporated by reference herein.

FIELD OF THE INVENTION

The present invention relates to a device and method for detecting light allowing retrieval of a physiological parameter of a user carrying said device.

BACKGROUND OF THE INVENTION

Light based non-invasive monitoring devices of physiological parameter (or signal) rely on the light emission to a targeted body part, the light absorption/scattering proprieties of the tissue (including the blood) and the collection of the scattered or transmitted light. Every heart beat leads to a blood pulse in the body part, with an increased amount of blood and therefore an increased light absorption and thus a decreased collection of scattered/transmitted light by the light detector. The optical method to measure such blood volume changes is called photoplethysmography (PPG). Various vital signs can be derived from PPG, namely heart rate, respiration rate, blood oxygen saturation, and it might even be used as a surrogate measurement for blood pressure. When it is used to derive the blood oxygen saturation, the method is called pulse oximetry (SpO2). SpO2 sensors are widely used in hospital settings, whereas PPG heart rate measurements find applications in wearable devices as activity trackers or sports watches.

The emission of light into targeted tissue (or skin; both being used herein as meaning the same) is most commonly done by one or more LEDs or laser diodes (as light source), and the collection of light is most commonly done directly using a photosensor (as light sensor, such as a photodiode) close to the targeted tissue. Part of the light from the light source that has entered the tissue/skin comes back out of the tissue/skin after scattering in the tissue/skin. In known sensors, only a small part of that light is captured by the light sensor, while the rest of the light is lost.

US 2013/0131519 A1 discloses a monitoring device for the ear where the light is delivered to the ear canal through a light guide and where the light is collected from the ear region and guided to the optical detector. This enables sensing a position on the body difficult to access such as the inner ear. However, it suffers from low efficacy in light coupling into the light guide, loss within the guide and low light capture.

US 2015/094550 A1, EP 3020331 A1, and US 2007/129613 A1 disclose devices, in which a light source is equipped with a wavelength conversion means to alter the wavelength of the light emitted by the light source.

SUMMARY OF THE INVENTION

It is an object of the present invention to provide a device and method for detecting light allowing retrieval of a physiological parameter of a user carrying said device with an increased light sensing efficiency and efficacy.

In a first aspect of the present invention a device for detecting light allowing retrieval of a physiological parameter of a user carrying said device is presented, said device comprising:
a light source arranged for emitting light of at least a first wavelength into tissue of the subject,
a wavelength converter arranged for receiving at least part of the emitted light after interaction of the emitted light with the tissue and for converting the received light into at least a second wavelength different from the first wavelength, and
a light sensor arranged for receiving light converted by said wavelength converter.

In a further aspect of the present invention a corresponding method is presented.

Preferred embodiments of the invention are defined in the dependent claims. It shall be understood that the claimed method has similar and/or identical preferred embodiments as the claimed device, in particular as defined in the dependent claims and as disclosed herein.

The present invention is based on the idea to improve the capture of the light scattered back from the tissue through a larger surface and detection by a (small) sensor. In particular, a wavelength converter is used in the optical path between the tissue and the light sensor to convert the wavelength of the light scattered back from the tissue to a different wavelength. The converted light is then guided within the wavelength converter to the light sensor.

In this invention, a wavelength converter is introduced, sometimes also referred to as luminescent concentrator or light concentrator. A wavelength converter is typically made of a glass doped with a fluorescent dye. The fluorescent dye converts the light into a longer wavelength emitted in all directions. A large part of the light is trapped in the material due to total internal reflection. Wavelength converters per se are generally known and e.g. described in U.S. Pat. No. 7,982,229 B2. In embodiments of the presented device such a known wavelength converter may be used.

Whereas in conventional PPG only about 1% of the light emitted from the light source to the skin is captured by the sensor although around 50% of the light emitted is scattered back from the skin, leading to a low and noisy signal, according to the present invention much more light can be captured (e.g. more than 20% or even more than 50%).

Further, with a conventional sensing device a high amount of power from the light source is required to obtain a good signal, thus limiting the battery life of a wearable device. Battery life is very important in nowadays wearables that should be worn continuously. Due to the improved efficiency of the presented device, battery life can be extended.

The light that is captured by the photodetector in a conventional sensing device comes from only a small part in the skin and depends very much on the local structure in the skin. Therefore it is prone to motion artefacts caused by shifting of the sensor over the skin. With the presented device a larger part of the skin is probed so that the motion artefacts are reduced.

The presented device does not simply use a larger sensor or multiple sensors to capture more light, which would add further limitations due to size, shape, cost and more complex electronics, but mere an additional wavelength converter is integrated into the device.

According to an embodiment said wavelength converter comprises a doped material arranged for converting the wavelength of the received light. For instance, a material doped with fluorescent dye or quantum dots may be used which can be easily implemented at low costs for the desired purpose. The material may e.g. be a light transmissive material such as crystalline, glass, ceramic or polymeric material.

The shape and/or material are preferably designed to guide the converted light within the wavelength converter. Preferably, a material with refractive index between 1.42 and 1.8, more preferably between 1.48 and 1.54, is used.

In an embodiment, the wavelength converter has a width selected to absorb more than 95% of the light source light, e.g. the wavelength converter may have a width selected from the range of 0.05-3 cm, especially 0.1-1.5 cm, such as 0.2-0.5 cm. With the preferably used fluorescent dye concentration, such width is enough to absorb substantially all light received from the tissue.

The wavelength converter is preferably configured to convert the received light into a second wavelength that is longer than the first wavelength. Longer wavelengths generally have a lower refractive index, so they may be less efficiently trapped in the wavelength converter. Further, the sensor should have good sensitivity for the detected wavelength and preferably low sensitivity for the emitted wavelength, which can also be supported with this embodiment.

The wavelength converter may further comprise one or more radiation input faces. These one or more faces are configured to receive light scattered from the tissue. The scattered light may provide light to a single face, or to a plurality of faces of the wavelength converter.

In another embodiment said wavelength converter is arranged between the light source and the light sensor, in particular for receiving light reflected from the tissue. It is preferably formed as a rod or cylinder and is arranged such that it receives light at a lateral side surface and emits converted light at a first front surface. In this way a compact design can be achieved.

In an alternative embodiment said wavelength converter is arranged at a distance from the light source for receiving light transmitted through the tissue. The device may e.g. be configured in the form of a finger clip making use of light that passed through the finger.

Preferably, the wavelength converter comprises a mirror at a first front surface and/or at a second front surface opposite the first front surface for internally reflecting the light. This further improves the efficiency. In case the first front surface is not totally covered by the light sensor, a mirror may be arranged at the first front surface.

The wavelength converter may also be made of a ceramic material, which generally has a large hardness and resistivity against chemicals.

Practically usable materials for the wavelength converter include one or more of the following materials:

glass-ceramics doped with $Mn^{2+}$, in particular one or more of garnets or cubic crystals doped/co-doped with $Mn^{2+}$, $Mn^{4+}$, $Ce^{3+}$, $Pr^{3+}$, $Eu^{3+}$, $Sm^{3+}$, $Eu^{2+}$, $Yb^{2+}$; non-cubic crystals, in particular phosphors doped with $Ce^{3+}$, $Pr^{3+}$, $Eu^{2+}$, $Yb^{2+}$; $Eu^{3+}$ incorporated into index-matching matrixes, in particular $TeO_2$, $SnO/P_2O_5$, or $Bi_2O_3$ containing glasses, high-index polyimide;

glass-ceramics doped with $Co^{3+}$, in particular one or more of garnets or cubic crystals doped/co-doped with $Ce^{3+}$, $Mn^{2+}$, $Mn^{4+}$, $Cr^{3+}$; non-cubic crystals, in particular phosphors doped with $Ce^{3+}$, $Pr^{3+}$, $Eu^{2+}$, $Yb^{2+}$, $Eu^{3+}$, $Tm^{3+}$, $Sm^{2+}$, $Cr^{3+}$, $Ti^{3+}$ incorporated into index-matching matrixes;

garnets or cubic crystals doped/co-doped with $Cr^{3+}$, $Nd^{3+}$, $Tm^{3+}$.

In one embodiment the wavelength converter comprises an outcoupling element, in particular a tapered outcoupling element, a lens, a fluid, a polymer, a glue, a gel or a collimator. This increases the transmission from the wavelength converter to the sensor and thus leads to a large signal output. The outcoupling element may be arranged at the first front surface, but may also be arranged on any other surface for practical reasons.

In an alternative embodiment the wavelength converter may be formed as a disk or ring, wherein the light source is arranged in a central area of the wavelength converter the light sensor is arranged at an edge of the wavelength converter.

The wavelength converter may also be a fiber or a multitude of fibers, for instance a fiber bundle, either closely spaced or optically connected in a transparent material. The fiber may be referred to as a luminescent fiber. The individual fiber may be very thin in diameter, for instance, 0.1 to 0.5 mm.

The light source preferably comprises one or more LEDs, arrays of LEDs, or lasers. For instance, in a practical embodiment for SpO2 measurements, the light source comprises two light source elements for emitting light at two different first wavelengths, in particular at a wavelength of visible light (e.g. red light) and a wavelength of infrared light (e.g. near-infrared light). In this case, the wavelength converter may also comprise two or more fluorescent dyes to convert the respective wavelength emitted by the respective light source element.

The device may further comprise an evaluation unit arranged for retrieving a physiological parameter of a user carrying said device from the light received by the light sensor. Thus, physiological information such as heart rate, respiration rate, pulse arrival, blood pressure, oxygen saturation, may be obtained.

Additionally, a dichroic mirror may be placed between the wavelength converter and the tissue in order to allow the light scattered from the tissue to reach the wavelength converter and prevent the converted light of being reemitted to the tissue.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
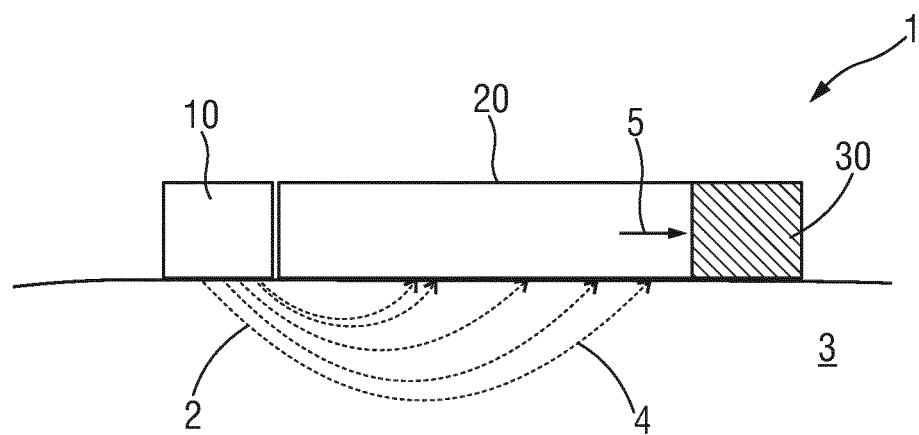
FIG. 1 shows a side view of a first embodiment of a device according to the present invention.

FIG. 1 shows a side view of a first embodiment of a device 1 according to the present invention. The device 1 comprises a light source 10 for emitting light 2 of at least a first wavelength into tissue 3 of the subject, a wavelength converter 20 for receiving at least part of the emitted light 4 after interaction of the emitted light 2 with the tissue 3 and for converting the received light 4 into at least a second wavelength different from the first wavelength, and a light sensor 30 for receiving light 5 converted by said wavelength converter 20.

Figure 2:
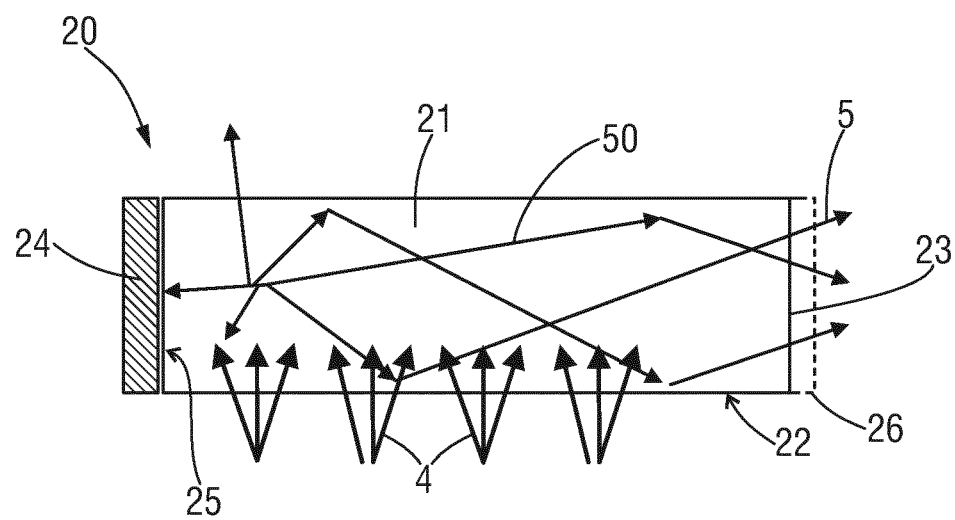
FIG. 2 shows a schematic diagram of an embodiment of a wavelength converter as used in an embodiment of the device according to the present invention.

FIG. 2 shows a schematic diagram of an embodiment of a wavelength converter 20 as used in an embodiment of the device according to the present invention. The wavelength converter 20 of this embodiment is formed as a plate, rod or cylinder and is made of a material 21 which is doped with fluorescent dye converting the wavelength of the light 4 to light 50 with a different, preferably longer wavelength and propagating in all directions. It is arranged such that it receives light 4 at a lateral side surface 22 and emits converted light 5 at a first front surface 23, also called outcoupling surface 23. The light 50 is thus maintained within the material 21 due to total internal reflection and can escape preferably only from the outcoupling surface 23. In this way the light intensity of the light 5 escaping from the outcoupling surface 23 is concentrated.

Optionally, a mirror 24 is placed at the opposite front surface 25 so that as much light as possible is reflected to the outcoupling surface 23.

The light source 10 is for example an LED, an array of LEDs, a laser, etc. The light 2, 4 passes through the sensed region 3, which can be skin or any other body tissue.

Using a wavelength converter allows converting almost all the light passing through the wavelength converter (independently of the direction of the light rays) into a second wavelength which will emit light in all directions. These light rays are then trapped inside the wavelength converter due to total internal reflection (in an exemplary implementation approx. 60% will remain in the wavelength converter).

In an embodiment the wavelength converter 20 is preferable made of a ceramic material. Advantages of this are that these materials have, in general, a very high hardness, are very stable, do not "wear" with respect to optical properties and show a large resistivity against chemicals, thus enabling cleaning in various ways (both chemically and mechanically). Furthermore, the compositions of these ceramics can be tuned in such a way, that the absorbing light matches the emitting spectrum of the light source 2 and the absorption spectrum of the targeted tissue 3.

Several exemplary potential materials are identified with various absorption/emission wavelengths that can provide the desired properties:

glass-ceramics doped with $Mn2+$; garnets and other cubic crystals (Spinel, perovskite, pyrochlore, etc.) doped/co-doped with $Mn2+$, $Mn4+$, $Ce3+$, $Pr3+$, $Eu3+$, $Sm3+$, $Eu2+$, $Yb2+$; non-cubic crystals, such as phosphors doped with $Ce3+$, $Pr3+$, $Eu2+$, $Yb2+$; $Eu3+$ incorporated into index-matching matrixes (e.g. $TeO2$, $SnO/P2O5$, or $Bi2O3$ containing glasses, high-index polyimide);

glass-ceramics doped with $Co3+$; garnets and other cubic crystals doped/co-doped with $Ce3+$, $Mn2+$, $Mn4+$, $Cr3+$; non-cubic crystals, such as phosphors doped with $Ce3+$, $Pr3+$, $Eu2+$, $Yb2+$, $Eu3+$, $Tm3+$, $Sm2+$, $Cr3+$, $Ti3+$ incorporated into index-matching matrixes;

garnets and other cubic crystals doped/co-doped with $Cr3+$, $Nd3+$, $Tm3+$.

Preferably, the concentration of luminescent sites (e.g. Ce) in the converter material 21 is high enough to have more than 99% conversion. That implies that the absorption length for the incident light 4 should be less than 0.22 times the plate thickness.

In other embodiments, an optional outcoupling element 26 may be provided at the first front surface 23 (shown with dashed lines in FIG. 2). The outcoupling element can e.g. have a tapered angle, e.g. in the range of 30° to 60°, e.g. of 45°. In another embodiment, the outcoupling of light from the wavelength converter 20 to the light sensor 30 can be enhanced using a fluid (such as oil, gel), a lens, a collimator as outcoupling element 26.

Figure 3:
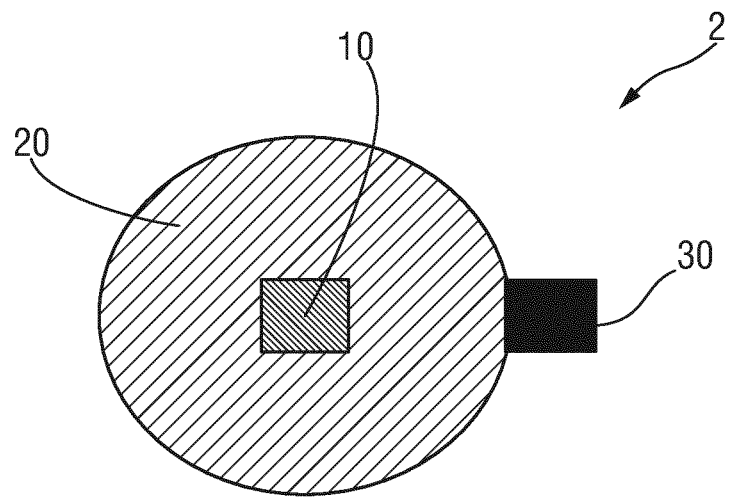
FIG. 3 shows a top view of a second embodiment of a device according to the present invention.

FIG. 3 shows a top view of a second embodiment of a device 2according to the present invention. In this embodiment the light source 10 is in the middle surrounded by the wavelength converter 20 that has the form of a disk. The light sensor 30 is arranged on a circumferential side surface (edge) of the disk-shaped wavelength converter 20.

Figure 4:
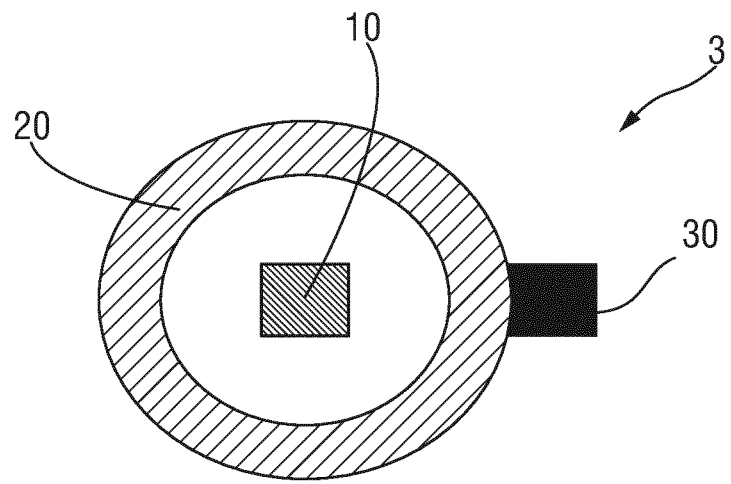
FIG. 4 shows a top view of a third embodiment of a device according to the present invention.

FIG. 4 shows a top view of a third embodiment of a device 3 according to the present invention. In this embodiment the wavelength converter 20 is formed in the shape of a ring to capture the light at a specific distance from the light source 10 in order to capture light having travelled deeper in the tissue.

Figure 5:
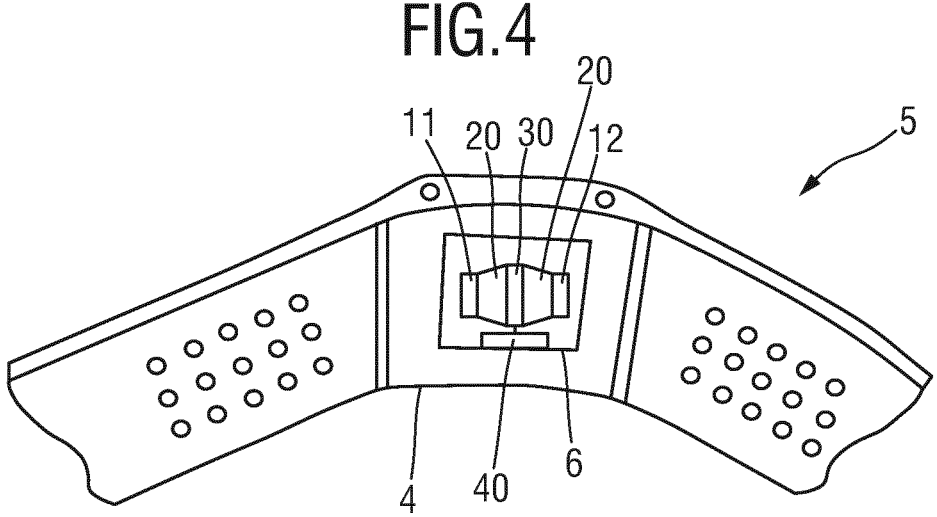
FIG. 5 shows a perspective view of a wrist watch including a fourth embodiment of a device according to the present invention.

The light source may contain an LED array including LEDs of different colors. Such an embodiment of a device 4 used in a wristwatch 5 is illustrated in FIG. 5. The device 4 is arranged at the lower surface 6 of the wristwatch so that it is in contact with the skin when worn by a user.

In this embodiment the light source is formed by two LEDs of different colors, in particular a first LED 11 emitting red light and a second LED 12 emitting infrared light. The light sensor 30 is in the central area and waveguide converters 20 are arranged between the LEDs 11, 12 and the light sensor 30.

It is known that adding one or more extra colors (with a different absorption coefficient in blood and/or a different penetration depth) can be used to reduce motion artefacts. Further, the use of at least two colors (having different absorption and/or scattering coefficients for oxygenated versus deoxygenated blood) is required for deriving the oxygen saturation in the blood. Although the wavelength converter changes the wavelength of the colors, this has no further implications, because the wavelength is changed only after it has been scattered by the skin (including the blood) and therefore, the information of interest has already been obtained before the wavelength is changed.

The light sensor 30 (and/or a processor evaluating the sensed signals) can distinguish between light originating from the first LED 11 and light originating from the second LED 12 by using the time at which the light is sensed, as usually in PPG sensors with LEDs of different colors, which alternate in their on and off states (i.e. when one LED is emitting light, the other is not and vice versa).

In another embodiment the device further comprises an evaluation unit 40, e.g. a processor, for evaluating the sensed signals and for retrieving a physiological parameter of a user carrying said device from the light received by the light sensor 30, i.e. the sensed signals. Such an optional evaluation unit 40 is also shown in FIG. 5 with dashed lines. In an alternative embodiment the sensed signals are transmitted (in a wired or wireless manner) to an external evaluation unit, e.g. to a smartphone, computer, laptop, patient monitor, etc. for further processing.

Figure 6:
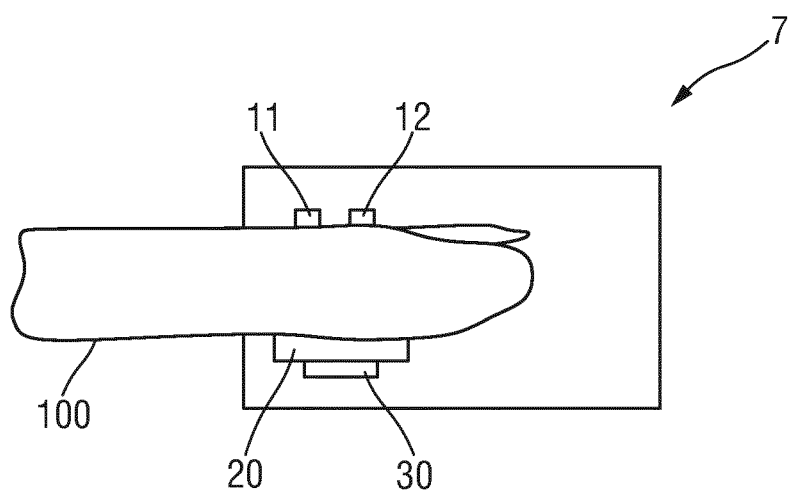
FIG. 6 shows a side view of a pulse oximeter representing a fifth embodiment of a device according to the present invention.

FIG. 6 shows a side view of a pulse oximeter 7 representing a fifth embodiment of a device according to the present invention. The pulse oximeter 7 is configured as finger clip for monitoring SpO2 of the subject. The two LEDs 11, 12 are arranged on a first side of the finger 100. The wavelength converter 20 and the photodiode 30 are arranged on the other side of the finger 100, i.e. light emitted by the LEDs 11, 12 is transmitted through the finger 100 and the received by the wavelength converter 20. The photodiode 30 is arranged on a lateral side of the wavelength converter 20 in this embodiment, from which the converted light is output.

Hence, the present invention is not limited to devices of a reflective type making use of light reflected from tissue, but can also be applied in device of a transmissive type making use of light transmitted through tissue. Also hybrid forms of devices may be used. For instance, in the embodiment shown in FIG. 6 the wavelength converter may be arranged around part or the complete finger to collect light scattered by the tissue in all directions.

Other embodiments may be envisaged for specific location of the body such as the nose and the ear where access is more difficult.

The present invention can be used for unobtrusive monitoring of physiological parameters such as heart rate, respiration rate, blood oxygen saturation and (a surrogate for) blood pressure. Applications range from healthy living (think of activity trackers and sports watches), to home monitoring of elderly, patients with chronic diseases and for hospital to home, to hospital use, such as in the ICU and OR.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for detecting light allowing retrieval of a physiological parameter of a user carrying said device, said device comprising:
    a light source arranged for emitting light of at least a first wavelength into tissue of the user;
    a wavelength converter arranged for receiving at least part of the emitted light after interaction of the emitted light with the tissue and for converting the received light into at least a second wavelength different from the first wavelength; and
    a light sensor arranged for receiving light converted by said wavelength converter;
    wherein said wavelength converter is formed as a rod or cylinder and is arranged such that it receives light at a lateral side surface and emits converted light at a first front surface.

2. The device as claimed in claim 1,
    wherein said wavelength converter comprises a doped material arranged for converting the wavelength of the received light.

3. The device as claimed in claim 2, wherein said doped material arranged for converting the wavelength of the received light comprises a material doped with fluorescent dye or quantum dots.

4. The device as claimed in claim 1,
    wherein said wavelength converter is configured to convert the received light into a second wavelength that is longer than the first wavelength.

5. The device as claimed in claim 1,
    wherein said wavelength converter is arranged between the light source and the light sensor.

6. The device as claimed in claim 5, wherein said wavelength converter is arranged for receiving light reflected from the tissue.

7. The device as claimed in claim 1,
    wherein said wavelength converter is arranged at a distance from the light source for receiving light transmitted through the tissue.

8. The device as claimed in claim 1,
    wherein said wavelength converter is made of a ceramic material.

9. The device as claimed in claim 1,
    wherein said wavelength converter is made of one of the following materials:
    glass-ceramics doped with $Mn^{2+}$; non-cubic crystals incorporated into index-matching matrixes;
    glass-ceramics doped with $Co^{3+}$; non-cubic crystals incorporated into index-matching matrixes;
    garnets or cubic crystals doped/co-doped with $Cr^{3+}$, $Nd^{3+}$, $Tm^{3+}$.

10. The device as claimed in claim 9,
    wherein said glass-ceramics doped with $Mn^{2+}$ comprises one or more of garnets or cubic crystals doped/co-doped with $Mn^{2+}$, $Mn^{4+}$, $Ce^{3+}$, $Pr^{3+}$, $Eu^{3+}$, $Sm^{3+}$, $Eu^{2+}$, $Yb^{2+}$; and
    wherein said non-cubic crystals comprise phosphors doped with $Ce^{3+}$, $Pr^{3+}$, $Eu^{2+}$, $Yb^{2+}$; and
    wherein said $Eu^{3+}$ incorporated into index-matching matrixes comprise_$TeO_2$, $SnO/P_2O_5$, or $Bi_2O_3$ containing glasses, high-index polyimide;
    wherein said glass-ceramics doped with $Co^{3+}$ comprises one or more of garnets or cubic crystals doped/co-doped with $Ce^{3+}$, $Mn^{2+}$, $Mn^{4+}$, $Cr^{3+}$; and wherein said non-cubic crystals comprise phosphors doped with $Ce^{3+}$, $Pr^{3+}$, $Eu^{2+}$, $Yb^{2+}$, $Eu^{3+}$, $Tm^{3+}$, $Sm^{2+}$, $Cr^{3+}$, $Ti^{3+}$ incorporated into index-matching matrixes.

11. The device as claimed in claim 1, wherein said wavelength converter comprises an outcoupling element.

12. The device as claimed in claim 11, wherein said outcoupling element comprises at least one of: a tapered outcoupling element, a lens, a fluid, a polymer, a glue, a gel, and a collimator.

13. The device as claimed in claim 1,
    wherein said light source comprises one or more LEDs, arrays of LEDs, or lasers.

14. The device as claimed in claim 1,
    wherein said light source comprises two light source elements for emitting light at two different first wavelengths.

15. The device as claimed in claim 14, wherein said two different first wavelengths comprise a wavelength of visible light and a wavelength of infrared light.

16. The device as claimed in claim 1,
    further comprising a processor arranged for retrieving a physiological parameter of a user carrying said device from the light received by the light sensor.

17. A device for detecting light allowing retrieval of a physiological parameter of a user carrying said device, said device comprising:
    a light source arranged for emitting light of at least a first wavelength into tissue of the user;

a wavelength converter arranged for receiving at least part of the emitted light after interaction of the emitted light with the tissue and for converting the received light into at least a second wavelength different from the first wavelength; and a light sensor arranged for receiving light converted by said wavelength converter;

wherein said wavelength converter comprises a mirror at a first front surface and/or at a second front surface opposite the first front surface for internally reflecting the light.

18. A method for detecting light allowing retrieval of a physiological parameter of a user carrying a device for detecting light, said method comprising:

emitting, using a light source, light of at least a first wavelength into tissue of the user, receiving at least part of the emitted light after interaction of the emitted light with the tissue, converting, using a wavelength converter of the device, the received light into at least a second wavelength different from the first wavelength, and receiving, by a light sensor, the converted light;

wherein said wavelength converter is formed as a disk or ring, wherein the light source is arranged in a central area of the wavelength converter the light sensor is arranged at an edge of the wavelength converter, or comprises a fiber or a multitude of fibers.

\* \* \* \* \*